(12) United States Patent
Attolino et al.

(10) Patent No.: US 8,198,455 B2
(45) Date of Patent: Jun. 12, 2012

(54) PROCESS FOR THE PREPARATION OF DEXLANSOPRAZOLE

(75) Inventors: Emanuele Attolino, Palagiano (IT); Vittorio Lucchini, Casorate Primo (IT)

(73) Assignee: Dipharma Francis S.r.l., Baranzate (MI) (IT)

( * ) Notice: Subject to any disclaimer, the term of this patent is extended or adjusted under 35 U.S.C. 154(b) by 210 days.

(21) Appl. No.: 12/619,896

(22) Filed: Nov. 17, 2009

(65) Prior Publication Data

US 2010/0125143 A1    May 20, 2010

(30) Foreign Application Priority Data

Nov. 18, 2008   (IT) ................ MI2008A2046

(51) Int. Cl.
*C07D 401/12*   (2006.01)
(52) U.S. Cl. .................................... 546/273.7
(58) Field of Classification Search ............... 546/273.7
See application file for complete search history.

(56) References Cited

U.S. PATENT DOCUMENTS

| 6,462,058 | B1 | 10/2002 | Fujishima |
| 6,664,276 | B2 | 12/2003 | Fujishima |
| 6,939,971 | B2 | 9/2005 | Fujishima |
| 7,285,668 | B2 | 10/2007 | Hashimoto |
| 2009/0163553 | A1 | 6/2009 | Fujishima |
| 2011/0028518 | A1* | 2/2011 | Kolla et al. ........... 514/338 |

FOREIGN PATENT DOCUMENTS

| AU | 88406/91 | 11/1990 |
| EP | 1277752 A1 | 1/2003 |
| EP | 1293507 A1 | 3/2003 |
| EP | 1552833 A1 | 7/2005 |
| ES | 2023609 | 1/1992 |
| ES | 2060541 | 11/1995 |
| WO | 9208716 A1 | 5/1992 |
| WO | 9602535 A1 | 2/1996 |
| WO | 2005054228 A1 | 6/2005 |
| WO | 2009088857 A1 | 7/2009 |
| WO | 2009117489 A1 | 9/2009 |

OTHER PUBLICATIONS

Kirk-Othmer Encyclopedia of Chemical Technology, vol. 8, p. 95-147 (2002).*

* cited by examiner

*Primary Examiner* — Patricia Morris
(74) *Attorney, Agent, or Firm* — Rothwell, Figg, Ernst & Manbeck, P.C.

(57) ABSTRACT

Process for the preparation of (R)-2-[[[3-methyl-4(2,2,2-trifluoroethoxy)-2-piridyl]methyl]sulfinyl]benzimidazole (Dexlansoprazole) and new intermediates useful in its preparation.

13 Claims, No Drawings

PROCESS FOR THE PREPARATION OF DEXLANSOPRAZOLE

FIELD OF THE INVENTION

The present invention relates to a process for the preparation of (R)-2-[[[3-methyl-4(2,2,2-trifluoroethoxy)-2-piridyl]methyl]sulfinyl]benzimidazole (Dexlansoprazole) and intermediates useful for its preparation.

BACKGROUND OF THE ART

Dexlansoprazole, namely (R)-2-[[[3-methyl-4(2,2,2-trifluoroethoxy)-2-piridyl]methyl]sulfinyl]benzimidazole, having formula (I), is the (R) enantiomer of Lansoprazole, which is a protonic pump inhibitor of the gastric parietal cells and therefore useful in therapy in the treatment of several disorders of the gastrointestinal tract.

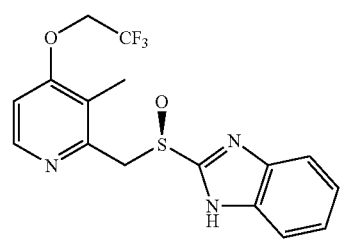
(I)

WO 96/02535 and EP 1277752 disclose the synthesis of Dexlansoprazole by stereoselective oxidation, according to the Kagan-Modena method, of the prochiral sulphur of formula (A) in toluene. Anyway, the stereoselective oxidation of the prochiral sulphur of formula (A), even if deeply studied, is a complex reaction when carried out on industrial scale and, generally, brings to the formation of a mixture of products comprising the sulphoxide of formula (I) having the desired stereochemistry, the enantiomer thereof, variable quantities of the staring sulphur of formula (A), and the superoxidation sulphur having formula (B).

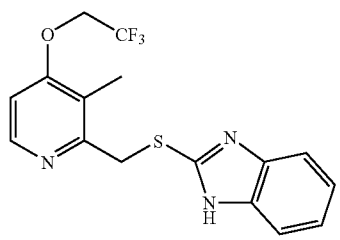
(A)

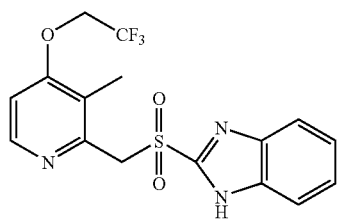
(B)

The purification of this mixture is often complicated and requires several crystallization steps to obtain a solid product sufficiently pure from a chemical and stereochemical point of view. In particular removal of the compound (B) is a known problem in the production of chiral sulfoxides and is a real issue in the preparation of chiral sulfoxides on industrial scale.

SUMMARY OF THE INVENTION

It has now been found a process for the preparation of Dexlansoprazole, or a salt thereof, which makes use of a sulphur intermediate of formula (III), as herein defined, which is cheap and largely available on the market. In particular the new process comprises the nucleophilic substitution of the nitro group in a compound of formula (II), as herein defined, and the stereoselective oxidation step of the starting compound of formula (III) as the last but one step of the synthesis. This makes the process of this invention more advantageous on industrial scale, when compared to the ones known in the art. In fact it allows preparing Dexlansoprazole on industrial scale, with a high chemical purity and substantially complete stereoselectivity and in an easy operating way.

DETAILED DESCRIPTION OF THE INVENTION

Object of the invention is a process for the preparation of a compound having formula (I), or a salt thereof,

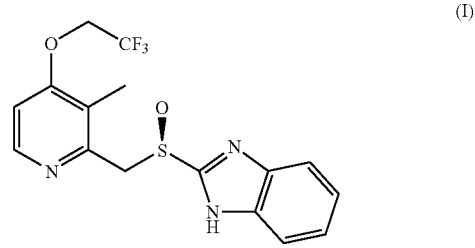
(I)

comprising a substitution reaction of the nitro group in a chiral sulfoxide of formula (II), or a salt thereof,

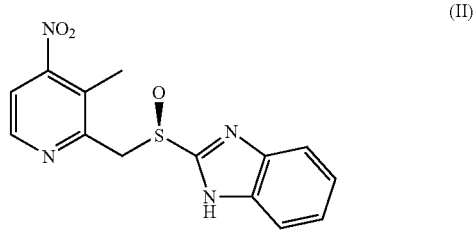
(II)

with 2,2,2-trifluoroethyl alcohol, in the presence of a strong base; and, if desired, the conversion of a compound of formula (I) into a salt thereof, or vice versa.

A strong base can be an organic or inorganic base.

A strong organic base can be, for example, a tertiary amine, in particular diisopropylethylamine, diazabicycloundecene or diaza-bicyclooctane; or a $C_1$-$C_6$ metal alcoholate, preferably an alkoxide of a tertiary alcohol of an alkaline metal or an alkaline earth metal for example calcium or barium alkoxide; more preferably potassium or sodium tert-butoxide. A strong inorganic base can be for example potassium carbonate, potassium phosphate or potassium hydroxide, preferably potassium hydroxide.

The amount of the base used, related to the compound of formula (II), or a salt thereof, can be stoichiometric or higher, in particular approximately from 1 to 10 equivalents of base, preferably from 4 to 6 equivalents can be used.

The reaction can be carried out using the same 2,2,2 trifluoroethyl alcohol as solvent; typically using at least a stoichiometric amount thereof. The reaction is preferably carried out in the presence of an excess of 2,2,2 trifluoroethyl alcohol, compared to the amount of compound of formula (II).

Alternatively, the same reaction can also be carried out in the presence of a palladium based catalyst, preferably made of a Pd(0) complex. Typically Pd(PPh$_3$)$_4$, Pd(dba)$_2$ or Pd(ter-Bu$_3$P)$_2$, preferably Pd(PPh$_3$)$_4$, wherein Ph means phenyl.

The molar ratio of catalyst used, related to the compound of formula (II), can be approximately comprised between 0.05 and 5%, preferably between about 0.1 and 0.5%.

The reaction can be carried out at a temperature comprised between 50° C. and 100° C., more preferably between about 70 and 95° C. In this range of temperature the reaction takes from 2 to 4 hours to be completed.

If desired, the compound having formula (I) can be converted in a salt thereof or vice versa according to known methods.

The recovery of the compound of formula (I), or a salt thereof, from the crude reaction mixture can be carried out according to known methods, for example by crystallization as known in the art. A solid compound of formula (I) is obtained, preferably as a crystalline sesquihydrate, or a salt thereof, with a purity equal to or higher than 99%, preferably equal to or higher than 99.9%; and an enantiomeric excess equal to or higher than 99.5% preferably equal to or higher than 99.8%.

The crystal particle size of a compound having formula (I), or a salt thereof, so obtained, is characterized by a D$_{50}$ value comprised between about 25 and 250 μm, wherein D$_{50}$ means the particle diameter so as to 50% (in volume) of the sample of particles has a diameter equal to or lower than the specific value. Such value, if desired, can be reduced for example by micronization or fine grinding according to known methods. The dimension of the particles can be defined with the known "laser light scattering" technique, using a Malvern Mastersizer MS1 instrumentation.

A chiral compound having formula (II), or a salt thereof, can be prepared by highly selective asymmetric oxidation of a prochiral compound of formula (III), or a salt thereof,

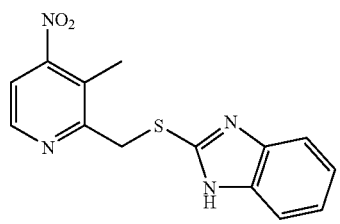

(III)

with an organic peroxide, in presence of a chiral titanium based catalyst and a base, and in a solvent wherein the compound of formula (III) is soluble.

A salt of a compound having formula (I), (II) or (III) is preferably a pharmaceutically acceptable salt.

An organic peroxide is for example tert-butyl hydroperoxide or cumene hydroperoxide, preferably cumene hydroperoxide.

A chiral titanium based catalyst can be obtained, for example, by adding a chiral binder to a titanium C$_1$-C$_6$ alkoxide. Preferably the titanium alkoxide is titanium isopropoxide.

The chiral binder can be, for example, an optically active diol having a suitable absolute stereochemistry, preferably a binder is a C$_1$-C$_4$ alkyl ester of the (+)-L-tartaric acid, more preferably (+)-diethyl-L-tartrate.

The molar ratio of the chiral titanium based catalyst used, related to the compound of formula (III), or a salt thereof, can be comprised between about 10 and 100%, preferably between about 10 and 40%.

The asymmetric oxidation reaction can be carried out in the presence of an organic base, such as for example a secondary amine in particular pirrolidine, piperidine or morpholine; or of a tertiary amine, in particular triethylamine, diisopropylethylamine, diazabicycloundecene, N-methyl morpholine; preferably diisopropyethyllamine.

A solvent wherein the compound of formula (III) is soluble is preferably an ether, typically tetrahydrofuran, dioxane, methyl-tertbutyl ether; or a mixture of two or more, preferably two or three of said solvents. More preferably the reaction is carried out in tetrahydrofuran. The dissolution of the compound (III) in the solvent can be carried out by heating, if the case till reflux temperature.

According to a particularly preferred embodiment of the invention the ratio between the compound (III) and the ether solvent, in particular tetrahydrofuran, is about 1 g of compound (III)/10 ml of solvent.

The asymmetric oxidation can be carried out in the presence of water in the reaction environment.

The reaction can be carried out at a temperature comprised between about −10° C. and 10° C., more preferably between about −5° C. and 5° C. In this range of temperature the reaction is generally completed within 2 and 6 hours.

If desired, a compound having formula (II) can be converted in a salt thereof, or vice versa, according to known methods.

The recovery of the compound having formula (II) from the crude of the reaction can be carried out according to known methods, for example by precipitation or crystallization, and to obtain a solid state compound of formula (II), or a salt thereof, having a HPLC purity equal to or higher than 98%, preferably equal to or higher than 99% and an enantiomeric excess equal to or higher than 96%, preferably equal to or higher than 98%.

An optically pure compound having formula (II), or with an enantiomeric excess equal to or higher than 96%, typically equal to or higher than 98%, as obtainable by the process of the invention, is a further object of the invention.

The compound (III), and the salts thereof, are commercially available and cheap.

A further object of the invention is a pharmaceutical composition comprising Dexlansoprazole, or a pharmaceutically acceptable salt thereof, having a purity equal to or higher than 99%, and/or an enantiomeric excess equal to or higher than 99.5%, and/or one or more excipients and/or carriers. Such composition can be prepared according to known methods in pharmaceutical technique. Preferably a compound having formula (I) or a salt thereof, having crystal dimension characterized by a D$_{50}$ value comprised between 25 and 250 μm, is used in the preparation of the above mentioned composition.

The following examples illustrates the invention.

Example 1

Synthesis of the (R)-2-[[[3-methyl-4-nitro-2-piridyl]-methyl]sulfinyl]benzimidazole (II)

A mixture of 2-[[3-methyl-4-nitro-2-piridyl]methylthio] benzimidazole (10 g, 33 mmoles, containing 70 mg of water)

and (+)-diethyl-L-tartrate (3.02 g, 14.6 mmoles), in THF (100 ml) is brought to reflux temperature and maintained under stirring for 30 minutes. Titanium isopropoxide (1.89 g, 6.66 mmoles) is added and the mixture is maintained under stirring at reflux temperature till the formation of a clear solution is achieved. The solution is then cooled and added with diisopropylethylamine (1.42 g, 10.9 mmoles). After having achieved the range temperature between −5° C. and 0° C., the solution is treated by slow cooling with cumene hydroperoxide 88% (17.3 g, 100 mmoles). The reaction mixture is maintained under stirring for 3 hours at about 0° C., then treated with a 30% sodium thiosulphate solution to decompose the residue of cumene hydroperoxide. After the separation of the phases the aqueous phase is washed with toluene, and the gathered up organic phases and concentrated under reduced pressure. The oily residue so obtained is taken up with water and treated with sodium hydroxide 30% till pH 12. The so obtained mixture is treated with isopropyl acetate and a solution of sodium bisulfite 25% till pH 9 is added. The precipitated solid is then filtered off and washed with isopropyl acetate and copious water. 9.2 g of product are recovered with a yield of 80% and a chemical and stereochemical purity (determined by HPLC and chiral HPLC) equal to or higher than 98%.

Example 2

Synthesis of Dexlansoprazole (I)

A solution of a compound of formula (II) (10 g, 31.5 mmoles), obtained by Example 1, in 2,2,2-trifluoroethyl alcohol (50 ml) is treated with Pd(PPh$_3$)$_4$ (36 mg, 0.031 mmoles) and potassium tert-butoxide (17.6 g, 157 mmoles). The so formed solution is maintained under stirring at a temperature of 80° C. for 4 hours and then cooled at room temperature. The reaction mixture is then quenched in water, extracted with methylethylketone. The phases are separated and the organic one is first diluted with water and then brought to pH 9 by adding sodium bisulfite. The phases are separated and the organic one is concentrated under reduced pressure. The residue is dissolved in acetone and then crystallized by adding water slowly to the solution. The obtained crystals are filtered, washed with acetone and copious water. After drying about 11 g of crystalline sesquihydrate Dexlansoprazole (yield 90%), with a purity higher than 99% and an enantiomeric excess higher than 99.5% are obtained.

Example 3

Synthesis of Dexlansoprazole (I)

A solution of compound (II) (1.42 Kg) in 2,2,2-trifluoroethanol (6.40 L) is treated with potassium hydroxide (1.31 Kg). The reaction mixture is left to react at 90° C. for 1.5 hours and then cooled to 25° C. Water and toluene are added to the reaction mixture and the two newly formed phases are separated. Pure crystalline Dexlansoprazole sesquihydrate (1.56 Kg, 90% yield) can be isolated from the organic phase following the procedure reported in Example 2.

The invention claimed is:

1. Process for preparing a compound of formula (I), or a salt thereof,

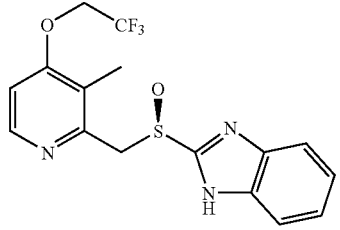

comprising a substitution reaction of the nitro group in a chiral sulfoxide of formula (II), or a salt thereof,

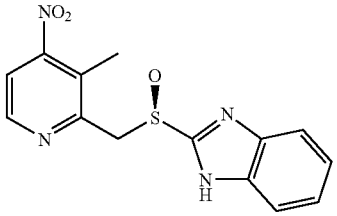

with 2,2,2-trifluoroethyl alcohol, in the presence of a strong base;

wherein the chiral sulfoxide of formula (II) or a salt thereof, is prepared by highly stereoselective asymmetric oxidation of a prochiral compound of formula (III) or a salt thereof

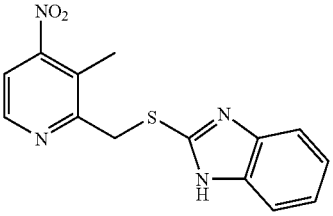

with an organic peroxide, in the presence of a chiral titanium based catalyst and a base, and in an ether.

2. Process according to claim 1, wherein the strong base is chosen from a tertiary amine, diazabicycloundecene, diazabicyclooctane, a $C_1$-$C_6$ metal alcoholate, potassium carbonate, potassium phosphate and potassium hydroxide.

3. Process according to claim 2, wherein the $C_1$-$C_6$ metal alcoholate is potassium or sodium tert-butoxide.

4. Process according to claim 2, wherein the strong base is potassium hydroxide.

5. Process according to claim 1, wherein the amount of base, related to the compound of formula (II), ranges from 1 to 10 equivalents of base.

6. Process according to claim 1, wherein the substitution reaction of the nitro group is carried out in the presence of a Pd based catalyst.

7. Process according to claim 6, wherein the catalyst is Pd(PPh$_3$)$_4$, Pd(dba)$_2$ or Pd(ter-Bu$_3$P)$_2$, in which Ph means phenyl.

8. Process according to claim 1, wherein the chiral catalyst is obtainable by adding a chiral ligand to a titanium $C_1$-$C_6$ alkoxide.

9. Process according to claim 1, wherein the base is a secondary or tertiary amine.

10. Process according to claim 1, wherein the base is diisopropylethylamine.

11. Process according to claim 1, wherein the ether is tetrahydrofuran.

12. Process according to claim 1, wherein the ratio between a compound of formula (III) and the ether is 1 g of compound of formula (III)/10 ml of ether.

13. The method according to claim 1, further comprising reacting the compound of formula (I) to form a salt thereof.

* * * * *